(12) United States Patent
Thielen et al.

(10) Patent No.: US 8,894,682 B2
(45) Date of Patent: Nov. 25, 2014

(54) PFO CLIP

(75) Inventors: Joseph M. Thielen, Buffalo, MN (US); Mark L. Jenson, Greenfield, MN (US); William J. Drasler, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1215 days.

(21) Appl. No.: 11/518,753

(22) Filed: Sep. 11, 2006

(65) Prior Publication Data

US 2008/0065149 A1 Mar. 13, 2008

(51) Int. Cl.
  *A61B 17/08* (2006.01)
  *A61B 17/00* (2006.01)

(52) U.S. Cl.
  CPC ... *A61B 17/0057* (2013.01); *A61B 2017/00867* (2013.01); *A61B 17/083* (2013.01); *A61B 2017/00606* (2013.01); *A61B 2017/00575* (2013.01); *A61B 2017/00592* (2013.01); *A61B 2017/00893* (2013.01)
  USPC .......................................... 606/213; 606/157

(58) Field of Classification Search
  USPC .......... 606/213, 151, 157, 158, 215, 216, 142
  See application file for complete search history.

(56) References Cited

U.S. PATENT DOCUMENTS

| | | | | |
|---|---|---|---|---|
| 6,911,037 | B2 * | 6/2005 | Gainor et al. | 606/213 |
| 2001/0034537 | A1 * | 10/2001 | Shaw et al. | 606/213 |
| 2002/0169475 | A1 * | 11/2002 | Gainor et al. | 606/213 |
| 2003/0225421 | A1 | 12/2003 | Peavey et al. | |
| 2004/0073242 | A1 | 4/2004 | Chanduszko | |
| 2004/0210301 | A1 * | 10/2004 | Obermiller | 623/1.24 |
| 2005/0043759 | A1 | 2/2005 | Chanduszko | |
| 2005/0059984 | A1 * | 3/2005 | Chanduszko et al. | 606/151 |
| 2005/0131460 | A1 | 6/2005 | Gifford, III et al. | |
| 2005/0192627 | A1 | 9/2005 | Whisenant et al. | |
| 2005/0234509 | A1 | 10/2005 | Widomski et al. | |
| 2005/0267495 | A1 | 12/2005 | Ginn et al. | |
| 2005/0267525 | A1 | 12/2005 | Chanduszko | |
| 2005/0273119 | A1 | 12/2005 | Widomski et al. | |

FOREIGN PATENT DOCUMENTS

| | | |
|---|---|---|
| EP | 1 281 355 A2 | 2/2003 |
| EP | 1179999 | 1/2006 |
| WO | WO 2004/069055 A2 | 8/2004 |
| WO | WO 2005/027752 A1 | 3/2005 |

OTHER PUBLICATIONS

International Search Report, Jan. 30, 2008, 17 pgs.
Japanese Office Action in related Japanese Patent Application No. 2009-528248 Jun. 19, 2012. 100 pgs.

* cited by examiner

*Primary Examiner* — Dianne Dornbusch
*Assistant Examiner* — Alexander Orkin
(74) *Attorney, Agent, or Firm* — Seager, Tufte & Wickhem LLC

(57) ABSTRACT

Embodiments for a device, system and method for occluding an opening in a septum. Embodiments of the device can include a first control component, a first elongate member that extends from the first control component, a second elongate member, a connecting member that positions the first elongate member adjacent the second elongate member and a retraction member releasably coupled to the first control component. The retraction member can be used to change a relative position of the first elongate member and the second elongate member of the device.

23 Claims, 9 Drawing Sheets

PFO CLIP

FIELD OF THE DISCLOSURE

The present disclosure relates to devices and methods for closing and/or occluding openings in septal structures.

BACKGROUND OF THE DISCLOSURE

During fetal development, a structure called the foramen ovate of the heart remains open to allow blood from the venous system to bypass the lungs and go to the systemic circulation. This is because prior to birth, the oxygenation of the blood in the fetus is via the placenta and not the lungs. A layer of tissue begins to cover the foramen ovale during fetal development, and typically seals over the foramen ovate soon after birth.

In a certain percentage of adults, however, the foramen ovale does not seal over. As a result, blood can flow directly between the atria of the heart. The blood flow can occur through direct openings between the atria and/or through a flap-like opening in the septum between the atria. In this latter case, elevation of pressure in the pulmonary circulation can cause blood to flow through the flap-like opening of the foramen ovate. This condition is known as a patent foramen ovale (PFO).

Typically, left atrial (LA) pressure is higher than right atrial (RA) pressure. As a result, the flap-like opening of a PFO usually remains closed. Under certain conditions, (e.g., pulmonary hypertension due to various causes, or transiently during a cough) right atrial pressure can exceed left atrial pressure. This pressure difference can create the possibility that blood and/or a blood clot could pass from the right atrium to the left atrium through the opening, allowing the blood clots to enter the arterial circulation. This is known as a paradoxical embolus because the blood clot paradoxially enters the arterial circulation instead of going to the lungs. Once in the arterial circulation, a blood clot could pass to the brain to result in a stroke. It is desirable that the possibility for this event to occur be eliminated.

Figure 1:
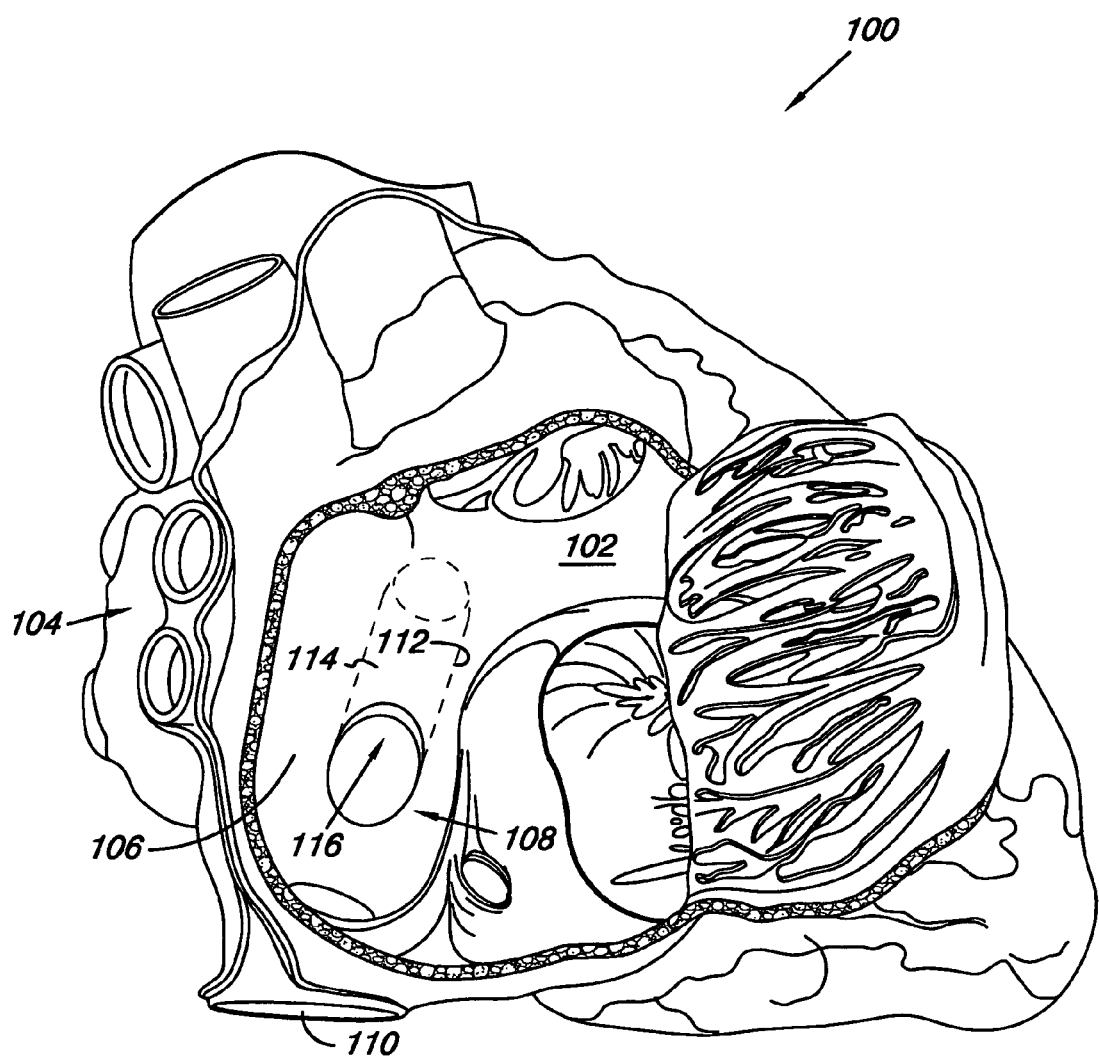
FIG. 1 illustrates a sectional view of a heart.

The illustrations provided in the Figures are not to scale.

DETAILED DESCRIPTION

Embodiments of the present disclosure provide for occluding an opening in a septum of the body. According to the various embodiments, a device of the present disclosure can occlude and/or close an atrial septal defect (ASD) and/or a patent foramen ovale (PFO) in the atrial septum of the heart. Embodiments of the device can be implanted through minimally-invasive techniques, where the device can be adjusted, repositioned and/or removed during delivery prior to deployment if needed. In one embodiment, adjusting, repositioning, and/or removing the device can occur up until the point that control component(s) are removed from the device, as will be discussed herein. Embodiments of the present disclosure can also be used to occlude and/or close other openings in the septal structures of the heart and/or openings in or at other anatomical locations of the body.

Embodiments of the present disclosure provide a device for occluding an opening in a septum, such as an ASD and/or a PFO. In one embodiment, the device is configured as a clip. As discussed herein, the clip can be configured to allow a compressive force to be applied across the wall(s) and/or membrane(s) of the septum. The compressive force provided by the device can draw together the wall(s) and/or membrane (s) of the septum, thereby helping to occlude and/or seal the passage through the septum. Coatings and/or a layer of material(s) can also be provided on the device for eliciting a biological response from the surrounding tissues, including the membranes defining the septum.

As discussed herein, the device for occluding an opening in the septum can include a first elongate member and a second elongate member joined by a connecting member. Embodiments of the device can be configured to have the connecting member position the first elongate member adjacent the second elongate member, where a profile of the device has an "S" or "Z" shape.

Embodiments of the device also include a control component. According to the present disclosure the control component includes a location along the first and/or second elongate member from which the relative position and/or state of the first and second elongate members can be adjusted and/or readjusted. In other words, the control component provides a location from which to move (e.g., bend, flex, shift, adjust, and/or readjust) the first elongate member and/or the second elongate member relative the other member.

In an additional embodiment, the control component can be used to retract the device once it has been deployed back into a lumen of a delivery catheter. In the various embodiments, force can be applied to the control component through a retraction member that extends through the delivery catheter. The retraction member can, in various embodiments, be releasably coupled to the control component.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Figure can also apply to the element shown in one or more additional Figures. Embodiments illustrated in the figures are not necessarily to scale.

FIG. 1 provides an illustration of a heart 100 having a right atrium 102 and a left atrium 104. An atrial septum 106 separates the right atrium 102 from the left atrium 104. The fossa ovalis 108 is situated at the lower part of the atrial septum 106, above and to the left of the orifice of the inferior vena cava 110.

The atrial septum includes a septum primum 112 and septum secundum 114 that overlap to occlude the foramen ovale. When a PFO is present, a PFO passage 116 extending between the septum primum 108 and septum secundum 110 exists. Because the blood pressure in the left atrium 104 is normally higher than in the right atrium 102, the septum primum 108 and septum secundum 110 usually stays closed. Under certain conditions, however, the right atrial blood pressure can exceed left atrial blood pressure, which can allow blood to pass through the PFO passage 112 from the right atrium 102 to the left atrium 104. As a result, it is possible that blood clot(s) could enter the arterial circulation that could lead to a stroke.

As discussed herein, embodiments of the present disclosure include a device to secure together, in one embodiment, the septum primum 112 and septum secundum 114 of a PFO. Once secured by the device, blood flow from the right atrium to the left atrium is minimized and/or prevented, thereby helping to reduce the risk of passing a blood clot into the arterial circulation. To accomplish this, the device can be positioned across the PFO passage 116 to draw the overlapping membranes of the septum primum 112 and the septum secundum 114 together, thereby occluding the PFO passage 116. The PFO passage 116 can be further be occluded by the presence of coatings and/or a layer of material on and/or between the connecting members.

Figure 2A:
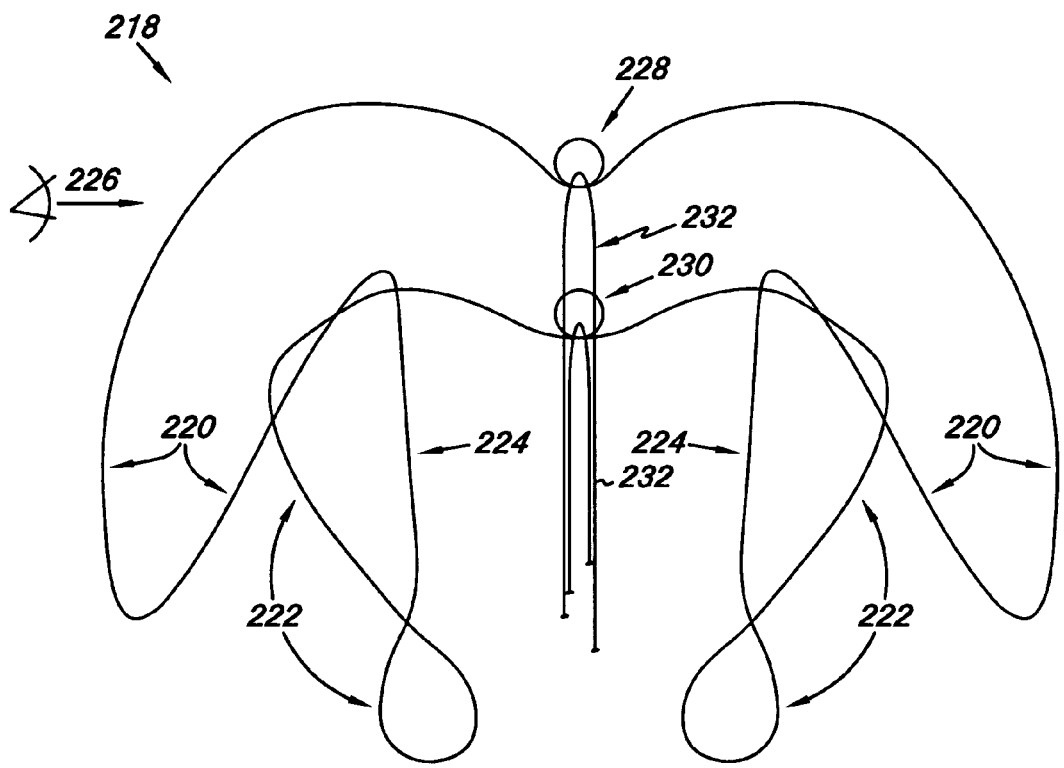
FIG. 2A illustrates an embodiment of a device according to the present disclosure.

FIG. 2A provides an embodiment of a device 218 for occluding an opening in a septum according to the present disclosure. As illustrated, device 218 includes a first elongate member 220, a second elongate member 222 and a connecting member 224. In one embodiment, the connecting member 224 is located between the first elongate member 220 and the second elongate member 222 to position the first elongate member 220 adjacent the second elongate member 222.

As illustrated, the first elongate member 220 overlies the second elongate member 222. The first and second elongate members 220, 222 of the device 218 are biased toward one another and, as shown in FIG. 2A, are connected by connecting members 224. The connecting members 224 can be relatively straight and are configured to pass through the PFO tunnel. In other embodiments, there may be a curve or a bend to the connecting members 224.

Figure 2B:
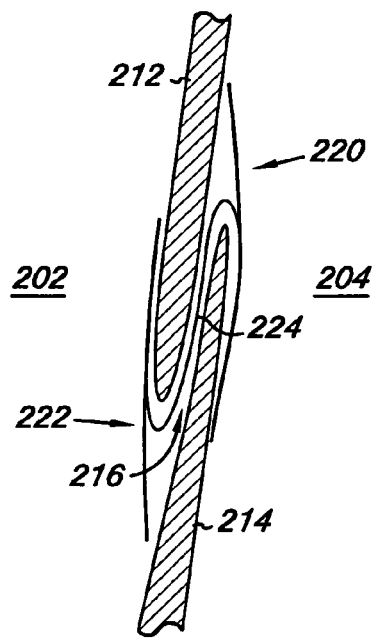
FIG. 2B illustrates the device of FIG. 2A positioned across a septal defect according to the present disclosure.

FIG. 2B provides a profile view of device 218 as seen from a view along 226. As illustrated, the device 218 in profile has a general "S" or "Z" shape. In one embodiment, this shape allows device 218 to be used as a PFO clip for joining the membranes 212 and 214 of a PFO. As illustrated, the first elongate member 220 can be located in the left atrium 204 and the second elongate member 222 can be located in the right atrium 202, such that the connecting member 224 extends through the PFO tunnel 216. As discussed herein, different configurations of the device 218, including positional relationships for the first and second elongate members 220, 222 and/or the connecting member 224, allow for a compressive force to be applied between the first and second elongate members 220, 222.

As illustrated in FIG. 2B, device 218 of the present disclosure can provide sufficient compressive force to compress and hold together the overlapping layers of the septum primum 212 and the septum secundum 214, thereby preventing the passage of blood (i.e., closing and/or occluding) the PFO passage 216. The first and second elongate members 220, 222 and the connection member 224 can have a number of different shapes and/or forms depending, in part, upon the distribution of force desired to effect closure of a septal opening, such as a PFO. The members 220, 222 and 224 of the device 218 can include configurations that allow the device 218 to be centered horizontally and/or vertically in the PFO passage 216.

The shape of each member can determine the location(s) at which the compressive force is applied to the overlapping layers of septal tissues 212, 214. In some embodiments, the compressive force can be concentrated at the center of the longitudinal distance of the PFO passage 216. In other embodiments, the compressive force can be distributed along the length of the passage 216. In still other embodiments, the compressive force can be applied toward the edges and/or the periphery of the PFO passage 216. Of course, the force may be a combination of the above-described forces.

The compressive force applied by the members 220, 222, and/or 224 of the various embodiments described herein may be adjusted in a variety of ways. For example, the thickness of the members 220, 222, and/or 224 may be increased or decreased to adjust the compressive force. In general (and with other design considerations similar), a thicker members 220, 222, and/or 224 can provide higher compressive force. Additionally, various member 220, 222, and/or 224 configurations may be chosen to increase the compressive force. Generally, bends with smaller angles will provide more compressive force. Alternatively, it is possible to have a wider portion elsewhere along member 220, 222 such that the device 218 is predisposed to bend into a certain shape and arrangement. Different parts of the device can be treated in a different manner to alter stiffness and recovery.

In addition, the cross-sectional shape of the members 220, 222, and/or 224 can change to allow for changes in the compressive force of the device. Examples of such cross-sectional shapes include, but are not limited to, circular or polygonal, for example square, or hexagonal. One skilled in the art will recognize the various design modifications that could be used to adjust the compressive force of the device.

As discussed herein, the device 218 can be adjusted, readjusted, manipulated, partially retracted, fully retracted, and/or removed through the use of at least a first control component 228 and/or a second control component 230. As illustrated, the first elongate member 220 forms and extends from the first control component 228 in an arcuate path to the connecting member 224. Similarly, the second elongate member 222 forms and extends from the second control component 228 in an arcuate path, albeit different than that of the first elongate member 220, to the connecting member 224.

In one embodiment, each of the first elongate member 220 and the second elongate member 222 extend from the connecting member 224 in an arcuate path so that the periphery of the first elongate member 220 and/or the second elongate member 222 is greater than that of the connecting member 224. In other words, the connecting member 224 connects and is located away from the periphery of the first elongate member 220 and the second elongate member 222.

In one embodiment, the first and/or second control components 228, 230 have a loop configuration as illustrated in FIG. 2A. The looped configuration of the control components 228, 230 can each receive a retraction member 232. In one embodiment, the retraction member 232 can pass through the control components 228, 230 to allow for a pulling force, as will be discussed herein, to be applied to one or both of the first and second control components 228, 230. Alternatively, the first and/or control component 228, 230 can be configured as a dimple and/or a deflection in the respective member to provide a location to which the pulling force can be applied through the retraction member 232.

As illustrated, the retraction member 232 can be releasably coupled to the first control component 228 and/or the second control component 230. In one embodiment, the retraction member 232 can be a filament having the flexibility to pass through and/or around one or both of the first and second control components 228, 230. The retraction member 232 also has a tensile strength sufficient to allow a pulling force applied at one end of the retraction member 232 to elastically deform the first elongate member 220 and/or the second elongate member 222. For example, a pulling force applied through the retraction member 232 can be used to change a relative position of the first elongate member 220 and/or the second elongate member 222 of the device 218.

As discussed more fully herein, the pulling force provided through the retraction member 232 can also be used to adjust, manipulate, retract and/or partially retract the first elongate member 220 and/or the second elongate member 222 during and/or following the deployment of device 218. The retraction member 232 can also be used to remove the device 218 from the heart. Examples of suitable materials for the retraction member 232 include, but are not limited to, metals, metal alloys, polymers, and/or combinations thereof. The retraction member 232 may also include multiple filaments configured in a cord, braided and/or woven manner. In addition, more than one retraction member 232 can be used with the embodiments of the present disclosure. For example, as discussed herein each of the control elements can have separate retraction members 232.

The members 220, 222, and 224 of the device 218 described herein can be constructed of one or more of a number of materials having elastic properties and in a variety of configurations. For example, the members 220, 222, and 224 can be formed from one or more of a biocompatible metal, metal alloy, polymer-coated metals or metal alloys, nonmetallic material, polymeric material, bioabsorbable polymer, or combination thereof. Specific examples of such materials include, but are not limited to, medical grade stainless steel (e.g., 316L), titanium, tantalum, platinum alloys, niobium alloys, cobalt alloys, alginate, or combinations thereof. Additional material examples include shape-memory materials, such as shape memory plastics, polymers, and thermoplastic materials. In one embodiment, shape memory alloys having superelastic properties generally made from ratios of nickel and titanium, commonly known as Nitinol, are also possible materials. Other materials are also possible.

The members 220, 222, and 224 of the device 218 can be formed of a single piece of material. For example, the device 218 could be formed from a single elongate member (e.g., a wire) that is bent into one of the device configurations illustrated herein. Ends of elongate member could then be joined by various attachment techniques, including welding, heat adhesives, non-heat adhesives and other joining techniques suitable for in-vivo application.

In an alternative embodiment, the members 220, 222, and 224 of the device 218 could be cut from a single sheet, or tube, of material. The device 218 could then be bent into one of the device configurations illustrated herein to form the device. Alternatively, the device 218 could be formed from two or more pieces of material that are joined to form the device 218. The shape of the device 218, once formed, can then be heat set as needed. Those skilled in the art will recognize that the device could be made of a combination of materials. Those of skill in the art will be able to identify biocompatible materials suited for particular applications, and the manufacturing techniques that would be used to configure the material into specific designs.

One or more of the members 220, 222, and/or 224 can further include one or more radiopaque markers (e.g., rivets, tabs, sleeves, welds). For example, one or more portions of the members 220, 222, and/or 224 can be formed from and/or coated with a radiopaque material. Coating techniques for applying the radiopaque markers can include electroplating and/or dipping one or more locations of the members 220, 222, and/or 224. Examples of radiopaque material include, but are not limited to, gold, tantalum, and platinum. Other radiopaques materials and application techniques are also possible.

Figure 3:
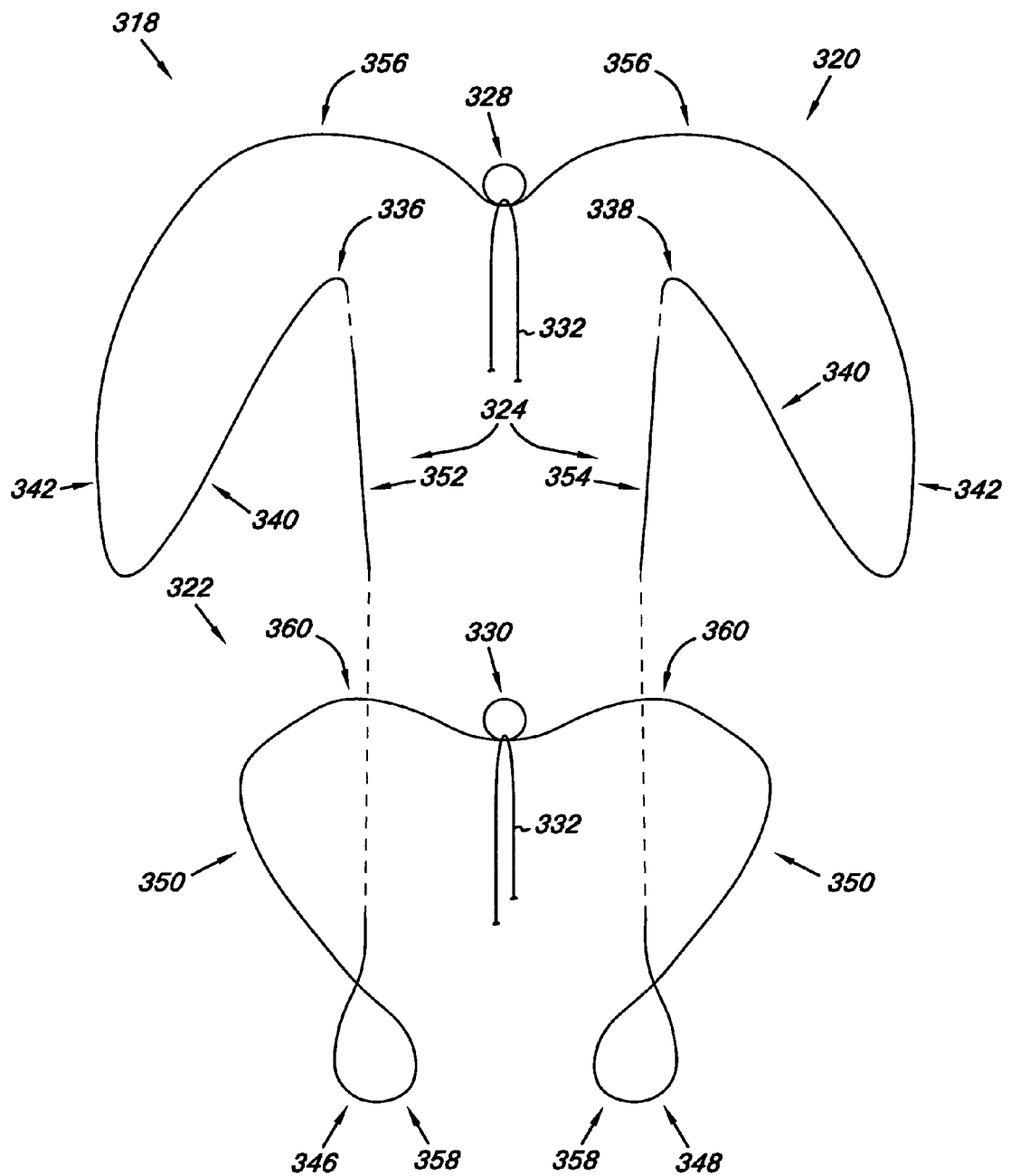
FIG. 3 illustrates an embodiment of a device in an exploded view according to the present disclosure.

FIG. 3 provides an illustration of the device 318 in an exploded view to illustrate the different portions and/or parts of the device 318. As discussed herein, the device 318 can be used as a PFO clip for joining the membranes that define the PFO. The device 318 includes the first elongate member 320, the second elongate member 322 and the connection member 324. The members 320, 322, and 324 each include portions and/or parts that allow the device 318 to be adjusted, readjusted, manipulated, partially retracted, fully retracted, and/or removed.

As illustrated, the first elongate member 320 includes a first elbow 336 and a second elbow 338. Each of the elbows 336, 338 also include a lever arm 340 that extends in an opposite direction, relative each other, to a pull member 342. Both pull members 342 then return to meet at the first control component 328. As discussed herein, a first retraction force (e.g., a pulling force) supplied through the retraction member 332 causes the lever arm 340 to pivot at the first elbow 336 and the second elbow 338 as the pull member 342 draws each lever arm 340 toward the first control component 328.

The second elongate member 322 includes a first pivot portion 346 and a second pivot portion 348 each with a lobe portion 350 that extends in an opposite direction to meet at the second control component 330. As discussed herein, a second retraction force supplied through the retraction member 332 causes the pivot portions 346, 348 to swing past the respective lobe portions 350 as the second control component 330 moves towards the pivot portions 346, 348. As illustrated, the first and second control components 328, 330 have a looped configuration to receive at least one of the filament 332. Other configurations for the control components 328, 330, as discussed herein, are possible.

The connecting members 324 of the device 318 further includes a first connection member 352 that extends between the first elbow 336 and the first pivot portion 346. The connecting members 324 of the device 318 further includes a second connection member 354 that extends between the second elbow 338 to the second pivot portion 348, where the first and second members 352, 354 position the first and second elongate members 320, 322 adjacent each other, as discussed herein.

In one embodiment, the first and second connection members 352, 354 flare away from each other as they meet the first and second elbows 336, 338 and the first and second pivot portions 346, 348. This configuration allows the connection members to provide a horizontal centering function for the device 318. Specifically, the connection members may be designed to fit within the PFO tunnel such that there is little (or no) horizontal movement once the device is deployed. The connection members can also serve to pull the membranes defining the PFO tunnel taught thereby helping to maintain the PFO tunnel in a closed state. As will be appreciated, the length of the connecting members can be varied depending on the anatomy of the PFO being closed.

In an additional embodiment, the connection members 352, 354 can position the first member 320 and the second member 322 either directly opposing each other or so the members 320, 322 have an offset relative each other. The shape and arrangement of either or both of the members 320, 322 can be adjusted such that the compressive forces they apply are as directly opposing as possible. In particular embodiments, the perimeter of the first member 320 can be different than that of the second member 322 so as to better conform to the anatomy of the patient's heart.

In an alternative embodiment, however, it may be desirable to have the members 320, 322 at least partially opposing (i.e., with an offset) each other. For example, if the septal tissue surrounding aperture includes a disproportionately thick portion (e.g. septum secundum as compared to septum primum), an offset may be used to seat the device 318 more securely upon septal tissue. Moreover, an offset may allows each of members 320 and 322 to be centered around each side of an asymmetric aperture of a PFO.

Further, the first and/or second members 320, 322 may be bent in a concave configuration, while other member may be flat. Alternatively, non-planar configurations than can be tailored to apply sufficient compressive force for closing a variety of PFOs. Whatever the shapes and/or configuration of the members 320, 322 may be of varied sizes to facilitate delivery of the device 318 (e.g. to improve collapsibility of the device 318) and/or to enhance its securement at the delivery site. For example, the members 320, 322 can be sized to better conform with anatomical landmarks enhance securement of the device 318 to the septal tissue.

The first elbow 336 and the second elbow 338 extend laterally from the first connection member 352 and the second connection member 354 to the lever arm 340 that extends linearly in a direction towards the first and second pivot portions 346, 348. The pull member 342 extends from the lever arm 340 in an arcuate configuration to meet at the first control component 328. As illustrated, the arcuate configuration of the lever arms 342 each includes a first elongate member apex 356 relative the first and second elbows 336, 338, where the first control component 328 is positioned between the apexes 356 and the first and second elbows 336, 338.

As discussed herein, a pulling force applied to the first control component 328 can draw the first elongate member 320 back into its delivery catheter. As the pulling force is applied to the first control component 328 the elbows 336, 338 seat against the end of the delivery catheter to provide a location from which the member 320 bends as the first control component 328 is first drawn into the catheter followed by the lever arms 342 and then the lever arms 340. As the pulling force continues, the entire member 320 can be drawn into the delivery catheter.

As illustrated, the lobe portions 350 each include a second elongate member apex 360 relative the first and second pivot portions 346, 348, where the second control component 330 is positioned between the apexes 360 and the first and second pivot portions 346, 348. In addition, the first and second pivot portions 346, 348 each have a looped member 358 that passes over itself to join with the lobe portion 350. During delivery of the device 318 from the delivery catheter, the looped members 358 deflect radially to unfold as they swing or rotate past the lobe portions 350 in an orthogonal plane relative the longitudinal axis of the device 318. Similarly, when a second retraction force is applied through the retraction member 332 at the second control component 330 the looped member 358 once again deflect radially as they align with the lumen of the delivery catheter prior to being drawn in after the lobe portions 350.

Figure 4:
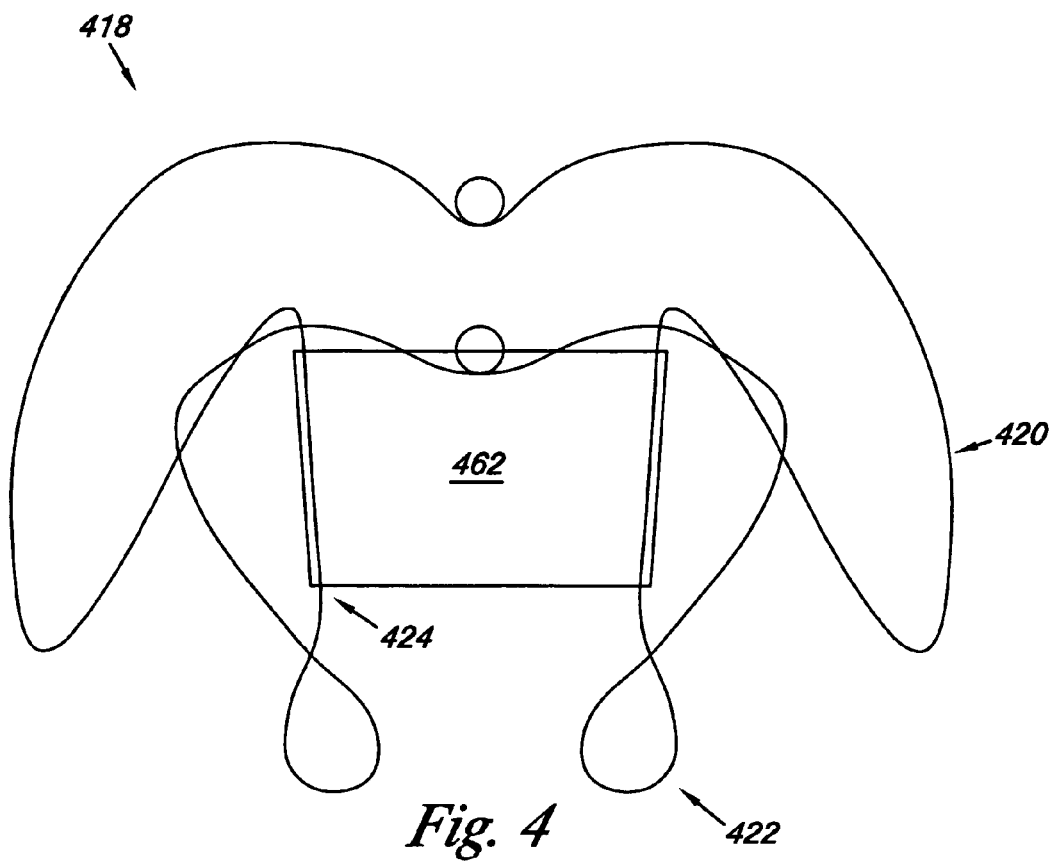
FIG. 4 illustrates an embodiment of a device according to the present disclosure.

In additional embodiments, the device 318 can be modified to encourage the anatomical closure of the overlapping layers of septal tissue. For example, as shown in FIG. 4, the device 418 can further include a layer of material 462 that extends between the first and second connection members 352, 354 in the PFO tunnel. In one embodiment, the material 462 can be a flexible material capable of promoting tissue in-growth. The materials may be formed by spinning, weaving, winding, solvent-forming, thermal forming, chemical forming, deposition, and combinations, include porous coatings, castings, moldings, felts, melds, foams, fibers, microparticles, agglomerations, and combinations thereof. Examples of such material include, but are not limited to, polymer based fabrics such as polyesters and/or Teflon-based materials, polyurethanes, other natural materials (e.g. collagen), or combinations thereof.

Figure 5:
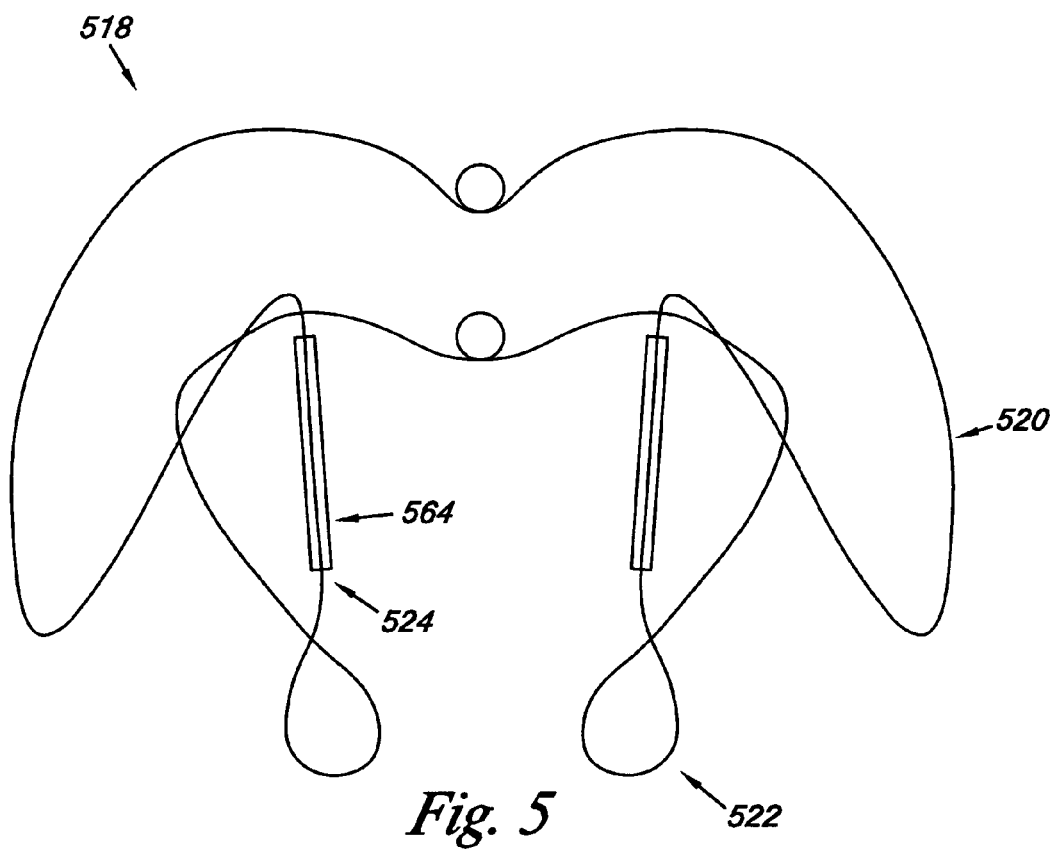
FIG. 5 illustrates an embodiment of a device according to the present disclosure.

In an additional embodiment, the device and/or the material 462 can further include coatings that can elicit a biological response (e.g., a bioactive agent). FIG. 5 provides an illustration of the device 518 that includes a coating 564. As will be appreciated, the coating 564 can be applied at one or more locations on the members 520, 522 and/or 524 of the device 518. In one embodiment, the coating 564 can include synthetic materials and/or biologic materials. Examples of synthetic materials include, but are not limited to: polyisobutylene-polystyrene (SIBS), polyurethane, poly(dimethylsiloxane) (PDMS), flouropolymer, proteins, polyethylene terephthalate (PET), protein analogs, copolymers of at least one of these materials, and other biologically stable and tissue-compatible materials.

Possible biologic materials and/or coatings include, but are not limited to, autologous, allogeneic, or xenographt material. These include explanted veins and decellularized basement membrane materials (such as non-crosslinked bladder membrane or amnionic membrane), such as small intestine submucosa (SIS) or umbilical vein. As will be appreciated, blends or mixtures of two or more of the materials provided herein are possible. For example, SIBS could be blended with one or more basement membrane materials.

The material and/or the coating may also be reinforced with high-strength materials. Examples of high-strength materials are nitinol, stainless steel, titanium, algiloy, elgiloy, carbon, cobalt chromium, other metals or alloys, PET, expanded polytetrafluoroethylene (ePTFE), polyimide, surlyn, and other materials known in the art. The high-strength materials may be in the form of wires, meshes, screens, weaves, braids, windings, coatings, or a combination. The high strength materials may be fabricated by methods such as drawing, winding, braiding, weaving, mechanical cutting, electrical discharge machining (EDM), thermal forming, chemical vapor deposition (CVD), laser cutting, e-beam cutting, chemical forming, and other processes known in the art. One embodiment includes CVD nitinol and wound or braided nitinol.

Suitable bioactive agents which may be incorporated with or utilized together with the material 462 or used as coating 564 may be selected from silver antimicrobial agents, metallic antimicrobial materials, growth factors, cellular migration agents, cellular proliferation agents, anti-coagulant substances, stenosis inhibitors, thrombo-resistant agents, stenosis inhibitors, antibiotic agents, anti-tumor agents, anti-proliferation agents, growth hormones, antiviral agents, anti-angiogenic agents, angiogenic agents, anti-mitotic agents, anti-inflammatory agents, cell cycle regulating agents, genetic agents, cholesterol lowering agents, vasodilating agents, agents that interfere with endogenous vasoactive mechanisms, and hormones, their homologs, derivatives, fragments, pharmaceutical salts thereof, and combinations thereof.

Suitable bioactive agents which may be incorporated with or utilized together with the coating and/or the material can also include diagnostic agents or media such as radiologic contrast materials, MRI contrast agents, ultrasound contrast agents, or other imaging aids such as iodinated or non-iodinated contrast media, metallic materials such as gold, iridium, platinum, palladium, barium compounds, gadolinium, encapsulated gas, or silica.

Examples of resorbable materials for use as the coating 564 and/or in the material 462 can include gelatin, alginate, PGA, PLLA, collagen, fibrin and other proteins. Materials such as elastin, acellular matrix proteins, decellularized small intestinal submucosa (SIS), and protein analogs, and certain polymers such as PTFE can perform multiple functions such as providing microporous material, bioresorption, and/or facilitation of elution of biologically active material.

To decrease the risk of thrombosis, thrombo-resistant agents for use with the coating and/or the material may be selected from the following agents: heparin, heparin sulfate, hirudin, hyaluronic acid, chondroitin sulfate, dermatan sulfate, keratan sulfate, PPack (dextrophenylalanine proline arginine chloromethylketone), lytic agents, including urokinase and streptokinase, including their homologs, analogs, fragments, derivatives and pharmaceutical salts thereof.

Also, anti-coagulants may be selected from the following: D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin, prostaglandin inhibitors, platelet inhibitors, tick antiplatelet peptides and combinations thereof.

In addition, suitable antibiotic agents include, but are not limited to, the following agents: penicillins, cephalosporins, vancomycins, aminoglycosides, quinolones, polymyxins, erythromycins, tetracyclines, chloramphenicols, clindamycins, lincomycins, sulfonamides, their homologs, analogs, derivatives, pharmaceutical salts and combinations thereof.

Anti-proliferative agents include, but are not limited to, the following: enoxaprin, angiopeptin, or monoclonal antibodies capable of blocking smooth muscle cell proliferation, hirudin, acetylsalicylic acid, and combinations thereof.

Suitable vascular cell growth promoters include, but are not limited to, transcriptional activators and transcriptional promoters.

Furthermore, anti-viral agents include, but are not limited to, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

Useful anti-inflammatory agents include agents such as: dexametbasone, prednisolone, corticosterone, budesonide, estrogen, sulfasalazine, mesalamine, and combinations thereof.

In one embodiment, an anti-mitotic agent may be radioactive material coupled to a biologically compatible carrier. In particular, the radioactive material may be selected from alpha-particle emitting isotopes and beta-particle emitting isotopes. Useful beta-particle emitting isotopes for treatment are generally selected from $^{32}P$, $^{131}I$, $^{90}Y$ and mixtures thereof.

In other embodiments, the bioactive agent(s) associated with the device 418 and/or the material 462 of the present disclosure may be a genetic agent. Examples of genetic agents include DNA, anti-sense DNA, and anti-sense RNA. DNA encoding one of the following may be particularly useful in association with an implantable device according to the present disclosure: (a) tRNA or rRNA to replace defective or deficient endogenous molecules; (b) angiogenic factors including growth factors such as acidic and basic fibroblast growth factors, vascular endothelial growth factor, epidermal growth factor, transforming growth factor alpha, transforming growth factor beta, platelet-derived endothelial growth factor, platelet-derived growth factor, tumor necrosis factor alpha, hepatocyte growth factor and insulin-like growth factor; (c) cell cycle inhibitors; and (d) thymidine kinase and other agents useful for interfering with cell proliferation.

The device 418 and/or the material 462 may also be treated and/or coated with any number of surface or material treatments. For example, the device 418 and/or the material 462 can be treated with one or more biologically active compounds and/or materials that may promote and/or inhibit endothelization and/or smooth muscle cell growth. Examples of such coatings include, but are not limited to, polyglactic acid, poly-L-lactic acid, glycol-compounds, and lipid compounds. Additionally, coatings can include medications, genetic agents, chemical agents, and/or other materials and additives. In addition, agents that limit or decrease cellular proliferation can be useful. Similarly, the device 418 and/or the material 462 may be seeded and covered with cultured tissue cells (e.g., endothelial cells) derived from a either a donor or the patient. The cultured tissue cells may be initially positioned to extend either partially or fully over the device 418 and/or the material 462. Additionally, coatings on device 418 and/or the material 462 may either prevent or facilitate tissue ingrowth there through, as the particular application for the device 418 may dictate.

FIGS. 6A-6E provide an illustration of a system 668 according to one embodiment of the present disclosure. The system 668 includes an elongate catheter 670 having a lumen 672 extending between a proximal end 674 and a distal end 676. The lumen 672 has a sufficient diameter to releasably house the device 618 to be used as a PFO clip in its elongated delivery form. The device 618 includes the first elongate member 620, the second elongate member 622 and the first and second connection members 652, 654, as discussed herein.

The system 668 further includes a push element 678 in the lumen 672 of catheter 670 that can be used to deliver the device 618 by pushing or extending it from the catheter 670. For example, the push element 678 could be used to push and/or hold the device 618 as the catheter 670 is retracted. In one embodiment, the push element 678 extends past the distal end 676 of the catheter 670 to allow application of a pushing or holding force to the member 678 to extend the device 618 from the catheter 670. In addition, the second retraction member 632 attached to the second control component 630 can pass inside the body of the push element 678 when the body of the push element 678 is a tube. This embodiment can help to control the location of the push element 678 with respect to the second control component 630, as well as to prevent tangling of the first and second retraction members 632. Other configurations are possible.

Figure 6A:
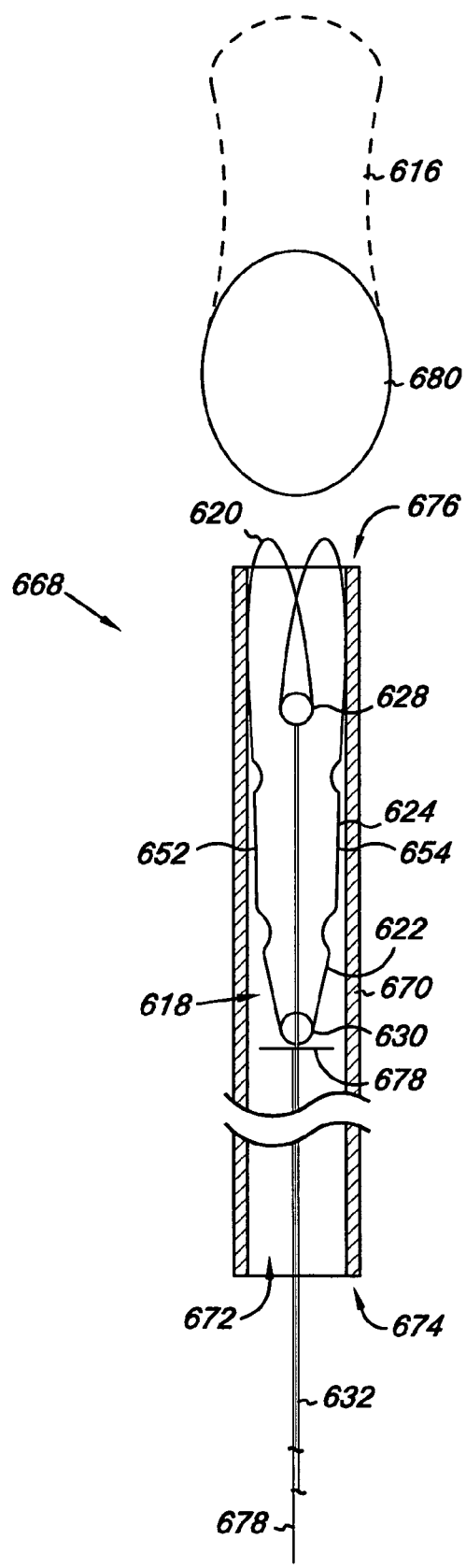
FIGS. 6A-6E illustrates an embodiment of a system that includes a device according to the present disclosure.
Figure 6B:
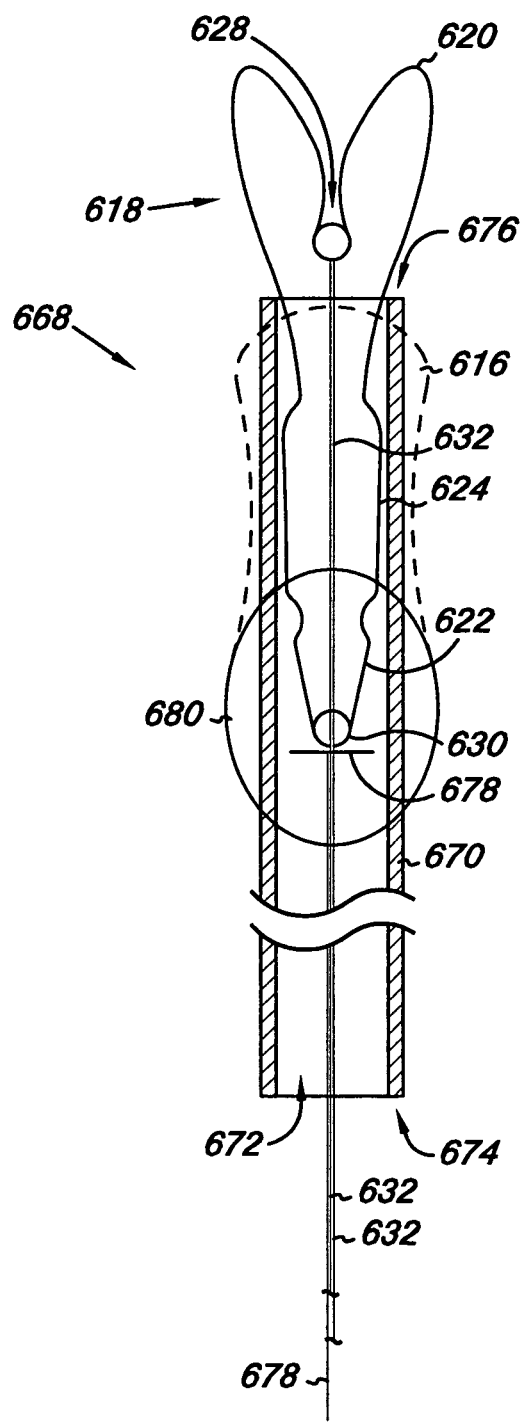
Figure 6C:
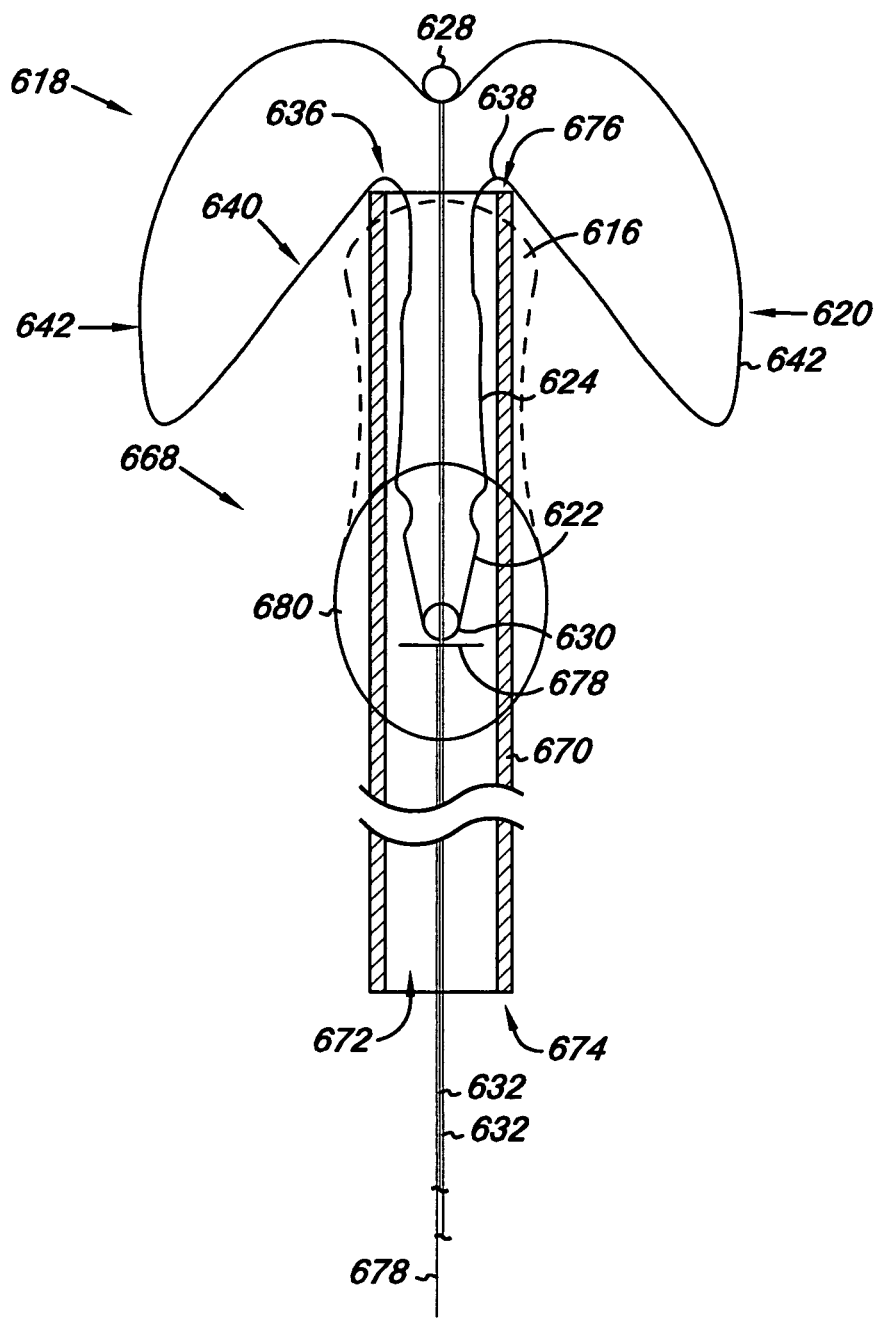

As illustrated in FIG. 6A, the distal end 676 of the catheter 670 can first be inserted into the right atrium of the patient's heart. The distal end 676 can then be passed through an aperture 680 located in the septal tissue (which, in this example, is a PFO tunnel 616) and into the left atrium. The first member 620 of the device 618 is then deployed into the left atrium, as shown in FIGS. 6B and 6C.

Following deployment of the first elongate member 620, the relative position of the member 620 can be adjusted and/or repositioned through the use of the retraction member 632. If a desired position for the first elongate member 620 cannot be achieved the first elongate member 620 can be retracted back into the lumen 672 of the catheter 670. For example, when adjusting and/or retracting the first elongate member 620 the first and second elbows 636, 638 of the first elongate member 620 can be seated against the distal end 676 of the catheter

670. Once seated, the first and second elbows 636, 638 are held stationary relative the distal end 676 of the elongate catheter 670.

A first retraction force (e.g., a pulling force) applied through the retraction member 632 can then move the first control component 628 causing the lever arm 640 to pivot as the first and second elbow 636, 638 elastically bend while the pull member 642 draws each lever arm 640 toward the first control component 628. As the first retraction force continues to be applied, the retraction member 632 draws the first control component 628 past the first and second elbows 636, 638 and into the lumen 672. As the first control component 628 enters the lumen 672, both the lever arms 640 and the pull members 642 elastically bend to be draw together into the lumen 672. As the lever arms 640 and the pull members 642 are drawn into the lumen 672 the first and second elbows 636, 638 are then also draw into the lumen 672 in an elastically deformed state. This retracted state for the device 618 is illustrated in FIG. 6A.

Figure 6D:
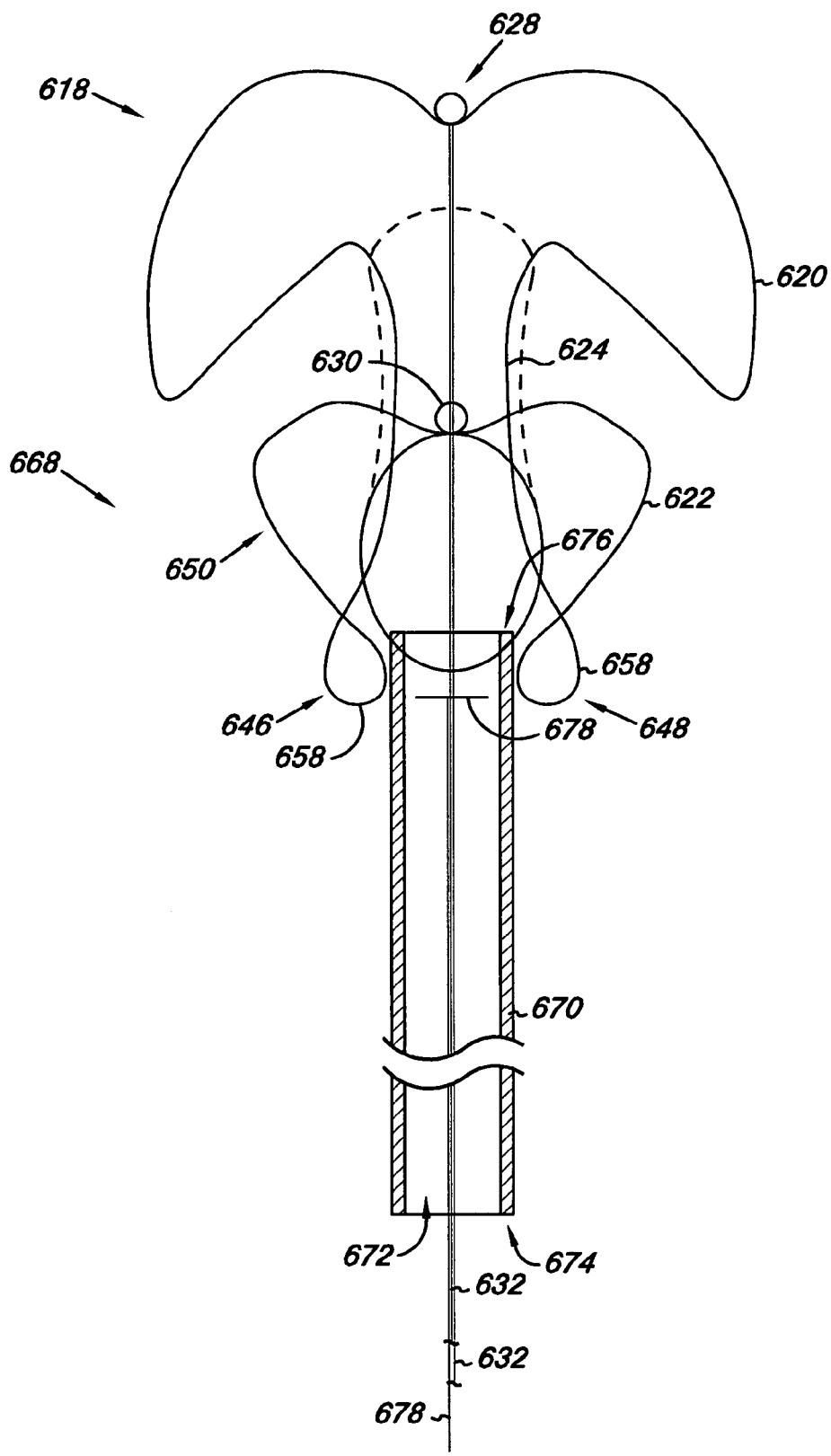
Figure 6E:
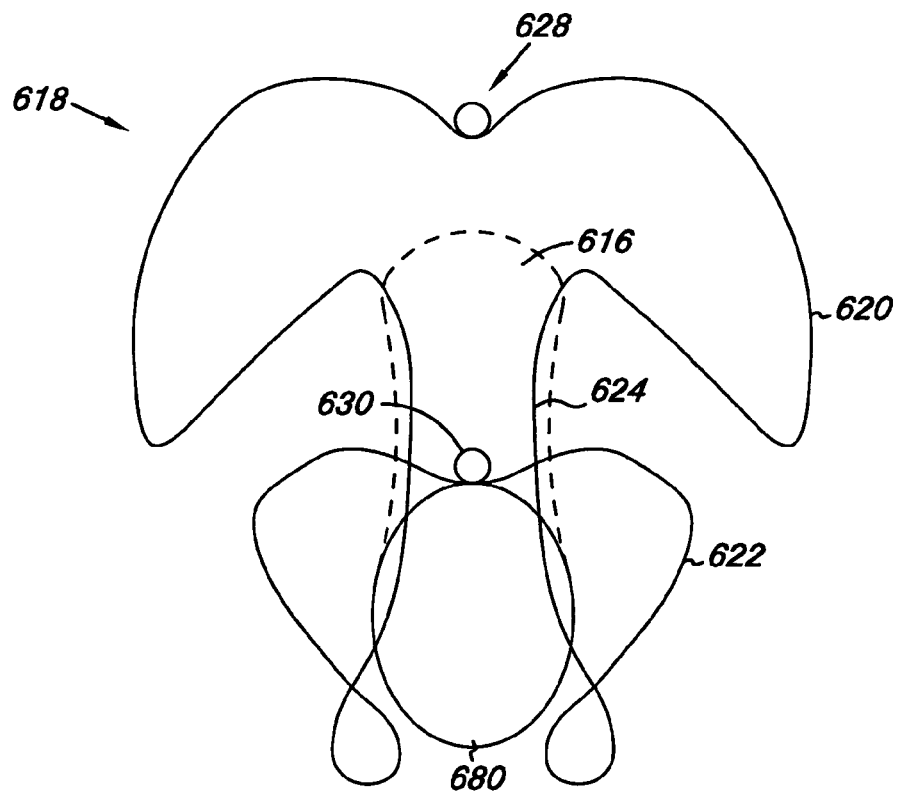
Figure 6E:
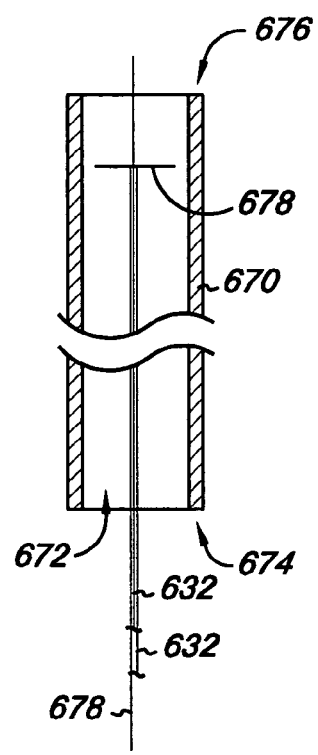

If, however, the desired position for the first elongate member 620 is achieved, the catheter 670 can then be withdrawn through the PFO channel 616 and into the right atrium as the connecting members 624 are deployed across the PFO channel 616. The second elongate member 622 can then be deployed into the right atrium 11 (FIGS. 6D and 6E). Following deployment, the relative position of the second elongate member 622 can be adjusted and/or repositioned through the use of the retraction member 632. When properly deployed, the device 618 is positioned across the PFO tunnel 616 with the first and second elongate member 620, 622 providing a compressive force against septum primum and septum secundum to close the PFO tunnel 616. The first and/or the second retraction member 632 can then be pulled through the control components 628, 630 to release the device 618. The retraction member(s) 632 and the delivery catheter 670 can then be withdrawn from the heart.

If, however, the desired position for the second elongate member 622 cannot be achieved the second elongate member 622, along with the first elongate member 620, can be retracted back into the lumen 672 of the catheter 670. As discussed herein, more than one retraction member 632 can be used with the device 618. For example, the system 668 can include the use of a first filament with the first control component 628, while a second filament, independent of the first filament, is used with the second control component 630.

In retracting the second elongate member 622, a second retraction force (e.g., a pulling force) can be applied to the second control component 630 through the retraction member 632 (e.g., a second filament) to draw the second elongate member 622 into the lumen 672 of the elongate catheter 670. As the second retraction force is applied, the first and second pivot portions 646, 648 elastically bend to pass in front of the lobe portions 650 as the second control component 630 moves towards the pivot portions 646, 648. As the second control component 630 is drawn into the lumen 672, the looped member 658 of the first and second pivot portions 646, 648 unfold along an arching path as they deflect radially, relative the long axis of the device, to rotate past the lobed portion 650. The first and second pivot portions 646, 648 are then drawn into the lumen 672 in an elastically deformed state. The remainder of the device 618 (e.g., the first elongate member 620) can then be drawn into the lumen 672 after the second control component 630 and the second elongate member 622, as discussed herein, and the catheter 670 removed from the body.

While the present disclosure has been shown and described in detail above, it will be clear to the person skilled in the art that changes and modifications may be made without departing from the scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A clip, comprising:
   a first elongate member having a first elbow and a second elbow each with a lever arm that extends in an opposite direction to a pull member that both return to meet at a first control component;
   a retraction member that contacts and encircles the first control component to create a first releasable coupling, where a first retraction force applied to the first control component via the retraction member causes the lever arm to pivot at the first elbow and the second elbow as the pull member draws each lever arm toward the first control component and the retraction member separates from the first control component to release the clip;
   a second elongate member having a first pivot portion and a second pivot portion each with a lobe portion that extends in an opposite direction to meet at a second control component, where the retraction member contacts and encircles the second control component to create a second releasable coupling and a second retraction force applied to the second control component via the retraction member causes the pivot portions to swing past the lobe portion as the second control component moves towards the pivot portions and the retraction member separates from the second control component to release the clip;
   a first connection member that extends between the first elbow and the first pivot portion; and
   a second connection member that extends between the second elbow to the second pivot portion, where the first and second connection members position the first elongate member adjacent the second elongate member.

2. The clip of claim 1, where the first elbow and the second elbow extend laterally from the first connection member and the second connection member to the lever arm that extends linearly in a direction towards the first and second pivot portions.

3. The clip of claim 2, where the pull member extends from the lever arm in an arcuate configuration to meet at the first control component.

4. The clip of claim 3, where the arcuate configuration of the lever arms each includes a first elongate member apex relative the first and second elbows respectively, where the first control component is positioned between the first elongate member apexes and the first and second elbows.

5. The clip of claim 1, where the first and second connection members flare away from each other as they meet the first and second elbows and the first and second pivot portions.

6. The clip of claim 1, where the first and second pivot portions each have a looped member that passes over itself to join with the lobe portion.

7. The clip of claim 6, where the looped members deflect radially to unfold as they swing past the lobe portions when the second refraction force is applied at the second control component.

8. The clip of claim 1, where the lobe portions each include a second elongate member apex relative the first and second pivot portions respectively, where the second control component is positioned between the second elongate member apexes and the first and second pivot portions.

9. The clip of claim 1, where the first and second control components have a looped configuration to receive the retraction member.

10. The clip of claim 1, including a coating on the first member and the second member.

11. The clip of claim 1, including a layer of material that extends between the first member and the second member.

12. A system, comprising:
an elongate catheter with a lumen extending between a proximal end and a distal end;
a clip releasably housed in the lumen of the elongate catheter, where the clip includes:
a first elongate member having a first elbow and a second elbow each with a lever arm that extends to a pull member that both meet at a first control component;
a second elongate member having first pivot portion and a second pivot portion each with a lobe portion that meet at a second control component;
a first connection member that extends between the first elbow and the first pivot portion;
a second connection member that extends between the second elbow to the second pivot portion;
a first filament that contacts and encircles the first control component to create a first releasable coupling, where the first filament can transmit a first retraction force to draw the first elongate member of the clip into the lumen of the elongate catheter and the first filament separates from the first control component to release the clip; and
a second filament that contacts and encircles the second control component to create a second releasable coupling, where the second filament can transmit a second retraction force to draw the second elongate member of the clip into the lumen of the elongate catheter and the second filament separates from the second control component to release the clip.

13. The system of claim 12, where the first elongate member of the clip extends from the distal end of the elongate catheter so that each lever arm extends radially in an opposite direction from the first and second elbows.

14. The system of claim 13, where the first and second elbows seat on the distal end of the elongate catheter.

15. The system of claim 14, where the first retraction force causes the lever arm to pivot at the first elbow and the second elbow as the pull member draws each lever arm toward the first control component.

16. The system of claim 15, where the first retraction force through the first filament draws both the lever arms and the pull members together into the lumen.

17. The system of claim 12, where the second retraction force causes the first and second pivot portions to pass in front of the lobe portions as the second control component moves towards the pivot portions.

18. The system of claim 17, where the first and second pivot portions each have a looped member that unfolds as they rotate past the lobed portion.

19. The system of claim 12, where the second control component retracts back into the lumen before the first and second pivot portions.

20. The system of claim 12, where the second filament can transmit the second retraction force to draw the first and second connection members into the lumen of the elongate catheter.

21. The system of claim 12, where the first control component retracts back into the lumen after the second control component and before the lever arms and the first and second elbows.

22. The system of claim 12, where the first filament contacts both the first control component and the second control component.

23. The system of claim 12, including a push element in the lumen of the elongate catheter, where the push element extends the clip from the lumen of the elongate catheter.

* * * * *